US00PP16189P2

(12) United States Plant Patent
Vlielander

(10) Patent No.: US PP16,189 P2
(45) Date of Patent: Jan. 3, 2006

(54) ***KALANCHOE* PLANT NAMED 'FIVERANDA PINK'**

(50) Latin Name: ***Kalanchoe guignardii*×*Kalanchoe blossfeldiana***
Varietal Denomination: Fiveranda Pink

(75) Inventor: Ike Vlielander, Maasland (NL)

(73) Assignee: Fides Goldstock Breeding B.V., DeLier (NL)

( * ) Notice: Subject to any disclaimer, the term of this patent is extended or adjusted under 35 U.S.C. 154(b) by 47 days.

(21) Appl. No.: 10/782,635

(22) Filed: Feb. 19, 2004

(51) Int. Cl.
*A01H 5/00* (2006.01)

(52) U.S. Cl. ..... Plt./339
(58) Field of Classification Search ..... Plt./339
See application file for complete search history.

*Primary Examiner*—Anne Marie Grunberg
(74) *Attorney, Agent, or Firm*—Mark P. Bourgeois

(57) ABSTRACT

A new cultivar of *Kalanchoe* plant named 'Fiveranda Pink' that is characterized by a compact habit, strong branching, long flower life, short response time, a large inflorescence and a uniform crop. In combination, these traits set 'Fiveranda Pink' apart from other known existing varieties of *Kalanchoe*.

1 Drawing Sheet

Botanical classification: *Kalanchoe guignardii*×*Kalanchoe blossfeldiana*.
Variety denomination: 'Fiveranda Pink'.

BACKGROUND OF THE INVENTION

The present invention relates to a new and distinct cultivar of *Kalanchoe* plant botanically known as *Kalanchoe guignardii*×*Kalanchoe blossfeldiana* and hereinafter referred to by the cultivar name 'Fiveranda Pink'.

The new cultivar is the product of a breeding program conducted by the inventor in a cultivated area of De Lier, The Netherlands. The objective of the breeding program is to develop new *Kalanchoe* cultivars with interesting and unique flower colors and shapes.

'Fiveranda Pink' is a hybrid that originated from the induced hybridization of the female or seed parent *Kalanchoe guignardii* (not patented) and the male or pollen parent *Kalanchoe blossfeldiana* 'Kerinci' (U.S. Plant Pat. No. 10,031). The cultivar 'Fiveranda Pink' was selected by the inventor in 2001 as a single plant within the progeny of the stated cross in a controlled environment of De Lier, The Netherlands.

Asexual reproduction occurred when terminal cuttings of the new cultivar 'Fiveranda Pink' were propagated in 2001 in De Lier, The Netherlands by the inventor. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Kalanchoe* cultivar 'Fiveranda Pink'. These traits in combination distinguish 'Fiveranda Pink' as a new and distinct cultivar apart from other existing known varieties of *Kalanchoe*.

1. *Kalanchoe* 'Fiveranda Pink' exhibits a compact habit.
2. *Kalanchoe* 'Fiveranda Pink' exhibits strong branching.
3. *Kalanchoe* 'Fiveranda Pink' exhibits a longer flower life.

4. *Kalanchoe* 'Fiveranda Pink' exhibits a short response time.
5. *Kalanchoe* 'Fiveranda Pink' exhibits a large inflorescence.
6. *Kalanchoe* 'Fiveranda Pink' exhibits a uniform crop.

The new cultivar 'Fiveranda Pink' is distinguishable from the female parent *Kalanchoe guignardii* by the following characteristics:

1. 'Fiveranda Pink' exhibits smaller leaves than *Kalanchoe guignardii*.
2. 'Fiveranda Pink' exhibits a larger inflorescence than *Kalanchoe guignardii*.
3. 'Fiveranda Pink' exhibits lighter pink flowers than *Kalanchoe guignardii*.
4. 'Fiveranda Pink' exhibits more branching than *Kalanchoe guignardii*.

The new cultivar 'Fiveranda Pink' is distinguishable from the male parent *Kalanchoe* 'Kerinci' by the following characteristics:

1. 'Fiveranda Pink' is larger than 'Kerinci'.
2. 'Fiveranda Pink' exhibits a larger inflorescence than 'Kerinci'.
3. 'Fiveranda Pink' exhibits a longer life as a potted plant.
4. 'Fiveranda Pink' does not require growth regulators.

BRIEF DESCRIPTION OF THE DRAWING

The accompanying photograph illustrates the distinguishing traits of *Kalanchoe* 'Fiveranda Pink'. The plant in the photograph shows an overall view of a 16 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Kalanchoe* cultivar named 'Fiveranda Pink'. Data was collected in De Lier, The Netherlands from 16 week glass greenhouse grown plants in 6 inch diameter containers. The time of year was Autumn and the temperature was kept at 20° Centigrade during the day and night. The light level was natural outdoor light. Photoperiodic treatments of 3 weeks of long days (more than 14 hours of light) followed by 8 weeks of short days (more than 14 hours of darkness) were used. No growth retardants were used. Color determinations are in accordance with The Royal Horticultural Society Colour Chart 2001 edition, except where general color terms of ordinary dictionary significance are used. The growing requirements are similar to the species. 'Fiveranda Pink' has not been tested under all possible conditions and phenotypic differences may be observed with variations in environmental, climatic, and cultural conditions, however, without any variance in genotype.

Botanical classification: *Kalanchoe* 'Fiveranda Pink'.
Use: Ornamental Annual.
Parentage: 'Fiveranda Pink' is a hybrid plant that resulted from the induced hybridization of the following parent plants:
*Female parent.*—*Kalanchoe guignardii.*
*Male parent.*—*Kalanchoe blossfeldiana* 'Kerinci'.
Vigor: Very Strong.
Growth habit: Upright.
Plant shape: Rounded, Triangular.
Suitable container size: 6 inch diameter container.
Height: 24 cm. in height.
Width: 35 cm. in width.
Low temperature tolerance: 12 degrees Centigrade.
High temperature tolerance: 35 degrees Centigrade.
Propagation: Terminal cuttings.
Time to initiate roots: 10–14 days to initiate roots at 21 degrees Centigrade.
Time to produce a rooted cutting or liner: 21–28 days at 21 degrees Centigrade.
Crop time: 11 to 14 weeks are required to produce a finished flowering plant.
Root system: Fine and fibrous.
Stem:
*Branching habit.*—Freely branching with shoots at every node.
*Average number of lateral branches.*—10–12.
*Pinching.*—Not Required.
*Lateral branch diameter.*—4–6 mm. in diameter.
*Lateral branch length.*—17–22 cm. in length.
*Lateral branch strength.*—Very strong.
*Stem color.*—147A.
*Pubescence.*—Absent.
*Internode length.*—4 cm. between nodes.
*Aspect.*—Upright.
Foliage:
*Texture.*—Both sides glabrous, coriaceous, succulent.
*Leaf arrangement.*—Opposite.
*Compound or singlet.*—Single.
*Quantity of leaves per lateral branch.*—8 to 13.
*Leaf shape.*—Ovate/Elliptic.
*Leaf apex.*—Acute to Obtuse.
*Leaf base.*—Acute.
*Leaf length.*—13 cm. in length.
*Leaf width.*—9.5 cm. in width.
*Pubescence.*—Absent.
*Leaf margin.*—Crenated.
*Young leaf color* (*lower surface*).—147B.
*Young leaf color* (*upper surface*).—147A.
*Mature leaf color* (*lower surface*).—147B.
*Mature leaf color* (*upper surface*).—147A.
*Vein color* (*lower surface*).—147A to 147B.
*Vein color* (*upper surface*).—147B.
*Leaf attachment.*—Petiolate.
*Petiole dimensions.*—20 mm. in length and 6 mm. in width.
*Petiole color upper side.*—147B.
*Petiole color lower side.*—147B.
Flower:
*Inflorescence arrangement.*—Single flowers arranged in racemes forming an umbel.
*Flowering habit.*—Continuous.
*Quantity of flowers per lateral stem.*—Approximately 40.
*Quantity of flower buds per lateral stem.*—Approximately 40.
*Quantity of flowers and buds per plant.*—Approximately 250.
*Natural flowering season.*—November/December in the Northern Hemisphere.
*Time to flower.*—10–12 weeks.
*Fragrance.*—None.
*Flower bud length.*—10 mm. in length.
*Flower bud diameter.*—2 mm. in diameter.
*Flower bud shape.*—Oblong to Ovate.
*Bud color.*—55C to 55D.
*Rate of bud opening.*—1 day.
*Flower aspect.*—Outward.
*Flower shape.*—Petals fused at base to form a bell shaped corolla.
*Flower dimensions.*—16 mm. in diameter and 14 mm. in height.
*Flower longevity.*—Approximately 22 days.
*Petal appearance.*—Shiny.
*Petal texture.*—Glabrous.
*Number of petals.*—4.
*Petal shape.*—Ovate.
*Petal margin.*—Entire.
*Petal apex.*—Acute.
*Petal dimensions.*—7 mm. in length and 4 mm. in width.
*Petal color when opening* (*upper side*).—55A.
*Petal color when opening* (*under side*).—55C.
*Petal color fully open* (*upper side*).—55B.
*Petal color fully open* (*under side*).—55C.
*Self-cleaning or persistent.*—Persistant.
Sepals:
*Number of sepals.*—Four.
*Sepal aspect.*—Upright, rigid.
*Sepal shape.*—Oblong/Pointed.
*Sepal margin.*—Entire.
*Sepal apex.*—Acute.
*Sepal base.*—Rounded.
*Sepal surface.*—Smooth, shiny.
*Sepal dimensions.*—6 mm in length and 2 mm. in width.
*Sepal color* (*upper side*).—138D.
*Sepal color* (*under side*).—138D.
Peduncle:
*Peduncle dimensions.*—7 mm. in length and 1 mm. in diameter.
*Peduncle aspect.*—Upright.
*Peduncle texture.*—Smooth.
*Peduncle color.*—138B.
*Peduncle strength.*—Strong.

Reproduction organs:

*Stamen number.*—8.

*Anther shape.*—Flat, Elliptic.

*Anther dimensions.*—0.3 mm. in length and 0.3 mm. in width.

*Anther color.*—150D.

*Amount of pollen.*—Low.

*Pollen color.*—12A.

*Pistil number.*—4.

*Pistil dimensions.*—1 mm. in length.

*Stigma shape.*—Flat.

*Stigma color.*—8D.

*Style length.*—10 mm.

*Style color.*—138D.

*Ovary color.*—138D.

Fruit:

*Fruit type.*—Capsule.

*Fruit dimensions.*—5 mm. in length and 1.5 mm. in width.

*Fruit color.*—165C.

Seed:

*Seed length.*—0.1 mm.

*Seed diameter.*—0.05 mm.

*Seed color.*—166C.

Disease and insect resistance: No disease problems observed, slight susceptibility to aphids.

It is claimed:

1. A new and distinct variety of *Kalanchoe* plant named 'Fiveranda Pink' as described and illustrated.

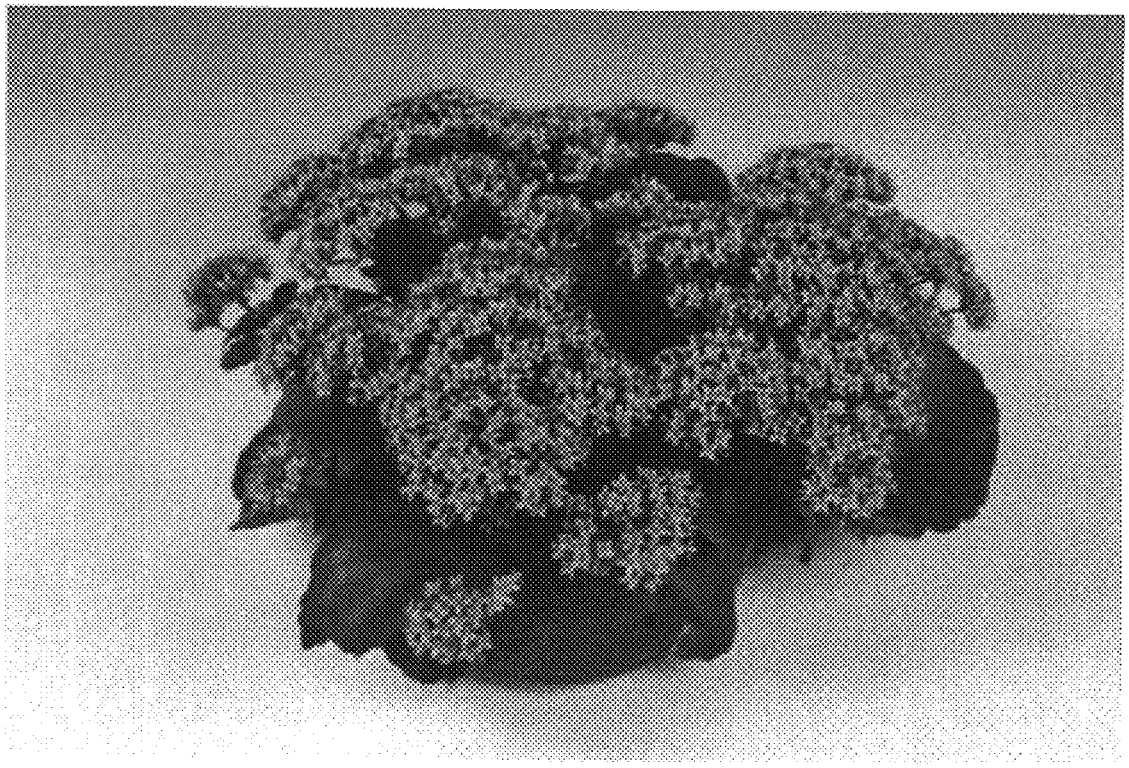

* * * * *